United States Patent [19]

Blum et al.

[11] 4,077,997
[45] Mar. 7, 1978

[54] DIPHOSPHONOALKANE CARBOXYLIC ACIDS, PROCESS OF PREPARATION AND METHODS OF USE

[75] Inventors: Helmut Blüm; Karl-Heinz Worms, both of Dusseldorf, Germany

[73] Assignee: Henkel Kommanditgesellschaft auf Aktien (Henkel KGaA), Dusseldorf-Holthausen, Germany

[21] Appl. No.: 761,271

[22] Filed: Jan. 21, 1977

[30] Foreign Application Priority Data

Jan. 21, 1976 Germany .............................. 2602030

[51] Int. Cl.$^2$ .......................... C07F 9/38; A61K 7/16; A61K 31/185
[52] U.S. Cl. ........................ 260/502.4 P; 71/DIG. 2; 210/58; 252/175; 252/8.6; 252/180; 252/389 A; 260/932; 424/49; 424/204
[58] Field of Search ........................... 260/502.4 P, 932

[56] References Cited

U.S. PATENT DOCUMENTS 3,093,672  6/1963  Miller ................................... 260/932
3,404,178  10/1968  Roy ............................. 260/502.4 P

FOREIGN PATENT DOCUMENTS 515,868  8/1955  Canada ................................. 260/932

*Primary Examiner*—Joseph E. Evans
*Attorney, Agent, or Firm*—Hammond & Littell

[57] ABSTRACT

Diphosphonoalkane carboxylic acids having the formula

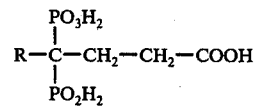

wherein R is H or —CH$_2$—CH$_2$—COOH; as well as their water-soluble salts. The compounds are excellent sequestering agents, especially for alkaline earth and earth metal ions. They are stabilizers for percompounds and are useful in the delaying of the setting times for gypsum. In addition, the compounds are useful in cosmetic preparations, such as toothpastes and mouthwashes where they prevent formation of tartar and plaque and are useful in therapy in the treatment of diseases related to the abnormal deposition or dissolution of difficultly soluble calcium salts in the animal body.

2 Claims, No Drawings

DIPHOSPHONOALKANE CARBOXYLIC ACIDS, PROCESS OF PREPARATION AND METHODS OF USE

The Related Art

Compounds of the oligocarboxylic alkane phosphonic acids type have gained in importance in recent times owing to their sequestering action. Compounds of this type are used as builder substances in cleaning agents, a substantial advantage residing in their satisfactory hardness stabilization with small dosages, particularly in the cleaning of containers and bottles. 2-phosphono-butane-1,2,4-tricarboxylic acid and 3-phosphono-pentane-1,3,5-tricarboxylic acid have proved to be particularly suitable in practice.

OBJECTS OF THE INVENTION

An object of the present invention is the obtaining of a diphosphonoalkane carboxylic acid selected from the group consisting of (A) a compound of the formula

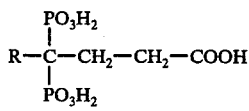

wherein R is selected from the group consisting of hydrogen and —CH$_2$—CH$_2$—COOH, and (B) a non-toxic, pharmacologically-acceptable water-soluble salt thereof.

Another object of the present invention is the development of a process for the production of the above-diphosphonoalkane carboxylic acid by reacting an ester of methylene diphosphonic acid with an ester of acrylic acid under alkaline conditions and hydrolyzing the resultant ester of diphosphonoalkane carboxylic acid.

A further object of the present invention is the development of a process for the delaying or inhibiting of the precipitation of alkaline earth metal ions from solution by the use of stoichiometric to sub-stoichiometric amounts of the above diphosphonoalkane carboxylic acids or their water-soluble salts.

These and other objects of the present invention will become more apparent as the description thereof proceeds.

DESCRIPTION OF THE INVENTION

The subject of the invention is new diphosphonoalkane carboxylic acids and water-soluble salts thereof. The said compounds are good complex formers and have further valuable properties with respect to their technical use.

Unexpectedly, it was found that the new diphosphonoalkane carboxylic acids described hereinafter have considerably better properties than the oligocarboxylic alkane phosphonic acids described by the prior art.

The new diphosphonoalkane carboxylic acids correspond to Formula I:

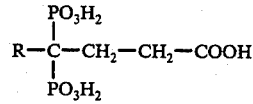 (I)

in which R = —H or represents —CH$_2$—CH$_2$—COOH, as well as their water-soluble salts. More particularly the present invention relates to a diphosphonoalkane carboxylic acid selected from the group consisting of (A) a compound of the formula

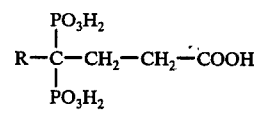

wherein R is selected from the group consisting of hydrogen and —CH$_2$—CH$_2$—COOH, and (B) a non-toxic pharmacologically-acceptable water-soluble salt thereof.

Compounds of the Formula I, in which R = —H, can be produced by reacting an acrylic acid ester with a methylene diphosphonic acid ester in the molar ratio of 1:1 in the presence of basic catalysts, such as, in particular, alkali metal lower alkanolates. The reaction product is then converted to the desired acid by saponification.

Diphosphonoalkane carboxylic acids of the Formula I, in which R = —CH$_2$—CH$_2$—COOH, are obtained in a similar manner by reacting an acrylic acid ester with a methylene diphosphonic acid ester in the molar ratio of at least 2:1 in the presence of basic catalysts, and subsequently saponifying the reaction product.

More particularly then, the processes are, respectively, a process for the production of the diphosphonoalkane carboxylic acid of Formula I wherein R is hydrogen, consisting essentially of reacting a lower alkyl ester of acrylic acid with a lower alkyl ester of methylene diphosphonic acid in a 1:1 molar ratio in the presence of a strong basic catalyst, saponifying the reaction product under aqueous acidic saponification conditions and recovering said diphosphonoalkane carboxylic acid where R is hydrogen, and a process for the production of the diphosphonoalkane carboxylic acid of Formula I, wherein R is —CH$_2$—CH$_2$—COOH, consisting essentially of reacting a lower alkyl ester of acrylic acid with a lower alkyl ester of methylene diphosphonic acid in at least a 2:1 molar ratio in the presence of a strongly basic catalyst, saponifying the reaction product under aqueous acidic saponification conditions and recovering said diphosphonoalkane carboxylic acid where R is —CH$_2$—CH$_2$—COOH.

The reactions are preferably conducted in the presence of a saturated solution of an alkali metal lower alkanolate in a lower alkanol, such as CH$_3$ONa/CH$_3$OH at an elevated temperature (due to the exothermic reaction). The saponification is preferably conducted in a heated acidic aqueous solution, such as refluxing concentrated hydrochloric acid.

The phosphonic acids described above can be converted to the corresponding non-toxic, pharmacologically acceptable, water-soluble salts by complete or partial neutralization with inorganic, organic or quaternary bases, such as alkali metal hydroxide, for example, NaOH, KOH, LiOH; alkali metal carbonates, such as Na$_2$CO$_3$; NH$_4$OH; lower alkylamines, such as methylamine; lower alkanolamines, such as monoethanolamine, diethanolamine, triethanolamine; and tetra-lower-alkyl-ammonium hydroxides, such as tetra-methylammonium hydroxide.

The new diphosphonoalkane carboxylic acids, including their alkali metal, ammonium or alkanolamine salts, are satisfactory complex formers for alkaline earth ions, preferably calcium ions, and can, therefore, be specifically used for water softening operations. It is unnecessary to work with stoichiometric quantities, and calcite precipitations can be considerably delayed by using sub-stoichiometric quantities.

Thus, they are eminently suitable as anti-corrosion and anti-scaling agents for cooling water, particularly combined with known additives, such as bivalent zinc and/or cadmium salts, orthophosphates, chromates or hydrazine hydrate.

The amount which is to be regarded as stoichiometric according to the compound which is used can be readily determined by a simple test. Theoretically, 1 mol of the compound should sequester up to 2 mols of calcium ions. In general, the complex formers are used in quantities of from 1 mol per 2,000 mols of metal ions up to six times the stoichiometric quantity.

Owing to the said properties, the new complex formers can also be used, for example, for the descaling of fabrics in which alkali salts have been deposited, and to reduce the ash concentration in fabrics. Furthermore, they are suitable for processes for cleaning rigid articles such as metal or glass. Their use as additive to bottle-rinsing agents is particularly important.

Advantageously, the complex forming capacity can also be used in systems in which copper ions have an undesirable influence. Examples of this which may be mentioned are the avoidance of the decomposition of percompounds or, alternatively, the stabilization of fats and soaps. Furthermore, the said compounds are suitable for use as additives to dyeing baths for textiles in order to bind, in a complex manner, those metal ions which form undesirable tints.

Finally, the complex forming capacity can also be used to feed so-called trace elements to plants. The satisfactory complex forming capacity of these compounds is also exhibited by the fact that the known red color, which is otherwise observed when adding rhodanide to solutions which contain tervalent iron, does not occur. Thus, these properties can also be used in an advantageous manner in order to prevent the depositing of iron compounds, particularly iron hydroxide, on fabrics or when washing bottles. The new compounds can also be used in galvanic baths instead of cyanides.

Finally, they are also suitable as builder substances with complexing properties in washing and cleaning agents and can be used in combination with known anionic, cationic or non-ionic, surface-active compounds. Furthermore, they can be used in combination with caustic alkalies, alkali metal carbonates, alkali metal silicates, alkali metal phosphonates, or alkali metal borates.

The diphosphonic acids which have been described are also suitable as active substances in pharmaceutical or cosmetic preparations which are used for the therapeutic or prophylactic treatment of disorders in the calcium or phosphate metabolism and the associated diseases. These diseases can be divided into two categories:

1. Abnormal depositions of difficultly soluble calcium salts, mostly calcium phosphate, cause bone malformations, pathological hardening of tissues and secretions in organs.
2. The abnormal dissolution of hard tissues causes losses of hard bone substance, which cannot be replaced or are replaced only by incompletely crystallized tissue. This dissolution is frequently accompanied by pathologically high calcium and phosphate concentrations in the plasma.

These diseases include: osteoporosis, osteodystrophy, Paget's disease, myositis ossificans, Bechterew's disease, cholelithiasis, nephrolithiasis, urinary calculus, hardening of the arteries (sclerosis), arthritis, bursitis, neuritis, tetany.

Instead of the free acids, their non-toxic pharmacologically acceptable salts, such as sodium, potassium, magnesium, ammonium and substituted ammonium salts, such as mono-, di or triethanol ammonium salts, are suitable for pharmaceutical use. The partial salts, in which only a portion of the acid protons is replaced by other cations, can be used as well as full salts, although partial salts, which react substantially neutral in aqueous solution (pH 5 to 9) are preferred. Mixtures of the aforesaid salts may also be used.

The dosage of the compounds used is variable and depends upon the prevailing conditions, such as the nature and the seriousness of the disease, the duration of the treatment and the particular compound. Individual doses can be from 0.05 to 500 mg per kg of body weight. The preferred dosage is 1 to 50 mg per kg of body weight per day and can be administered in up to four doses daily. Owing to the limited resorption, the higher dosages are required in the case of oral application. In the case of treatment over a long period of time, smaller doses are necessary after high initial doses in order to maintain the desired effect.

Doses of less than 0.05 mg/kg of body weight do not have any significant effect upon the pathological calcification or the resolution of calcified tissues. Long-term toxic side effects can occur in the case of doses in excess of 500 mg/kg of body weight. The described diphosphonic acids or their salts may be administered orally in the form of tablets or capsules, as well as subcutaneously, intramuscularly or intravenously in hypertonic solution. The preferred dosage ranges for these uses are (in mg/kg per day):

Orally 1.0 to 50.0
Subcutaneously 1.0 to 10.0
Intramuscularly 0.05 to 10.0
Intravenously 0.05 to 2.0

The substances can be formulated for administration in the form of tablets, pills, capsules or injection solutions.

They can be used in combination with the hormone calcitonine for the treatment of disorders of calcium or phosphate metabolism. Suitable calcitonines are synthetic and natural calcitonine obtained from pigs, cattle and salmon. It is also possible to use calcitonines whose biological efficacy has been changed by the substitution of individual amino acid groups in the peptide chain of the natural calcitonines which comprise 32 amino acids. Some of these calcitonines which have been mentioned are commercially available.

In the case of animals, the substances can also be used in fodder and as fodder additives.

When used in cosmetic preparations, such as mouthwashes and toothpastes, the diphosphonic acids in accordance with the invention or their pharmacologically harmless salts in concentrations of 0.01% to 5% by weight, prevent the formation of tartar or plaque.

Finally, the new diphosphonic acids are also suitable as an additive to preparations for producing $99^m$ technetium radio diagnostics. Diseases of the bones and tissues can be recognized and localized by radiography. The isotope technetium $99^m$, which has a half-life period of six hours, has been used for this purpose in recent times.

Convenient devices are available for its production, from which the radioactive isotope in the form of 99$^m$ pertechnetate can be obtained by elution with an isotonic solution of common salt.

Pertechnetate 99$^m$ differs from the radioactive fluorine or strontium previously used in that it does not combine specifically in the skeleton or in calciferous tumors in the body. It has to be reduced to a low oxidation stage for use and then has to be stabilized in this oxidation stage by means of a suitable complex former. Furthermore, the complex former must have a high selectivity for the preferred absorption by the skeleton or by calciferous tumors.

It has been discovered that the complexing diphosphonic acids described above, or pharmaceutically harmless water-soluble salts thereof, are particularly suitable for these purposes. The phosphonic acids are used together with a pharmaceutically acceptable tin (II), chromium (II) or iron (II) salt, the reducing salts being present in stoichiometric subordinate quantities relative to the phosphonic acids or water-soluble salts thereof. Thus, it is possible to produce, in a simple manner, a highly stable product which is suitable for sale in a solid form as tablets or in the form of a solution contained in an ampoule.

After the diphosphonic acid/reduced metal salt preparation has been added to a pertechnetate solution, the resultant complex forms a very effective means for diagnosing bone tumors, local disorders in bone metabolism and calciferous tissue tumors.

The present invention will now be further described by means of the following examples, which are not limitative in any manner.

EXAMPLE 1

57.6 gm (0.2 mol) of tetraethyl methylenediphosphonate and 34.4 gm (0.4 mol) of methyl acrylate were mixed and 12 to 14 ml of freshly prepared saturated CH$_3$ONa/CH$_3$OH solution were added drop by drop under agitation. The reaction temperature reached 90° C. Agitation was continued for 2 hours at 90° C to 100° C after the exothermic reaction had ceased. The reaction product was then subject to vacuum fractionation. The main fraction of the ester obtained had a boiling point of 210° C to 216° C/0.09 Torr. The density $n_D^{20}$ was 1.4513. The yield was 88%.

The ester obtained was subsequently saponified by refluxing for a long period of time with concentrated hydrochloric acid and the free acid was separated. The yield upon saponification was approximately 86%. In accordance with potentiometric titration, the diphosphonoalkane dicarboxylic acid of the formula

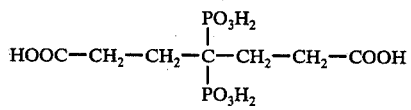

(I, R = —CH$_2$—CH$_2$—COOH) which was obtained had a molecular weight of 330 (calculated 320).

Analysis Values: Calculated: C 26.25% H 4.36% P 19.38%; Found: C 26.31% H 4.72% P 18.67%.

EXAMPLE 2

57.6 gm (0.2 mol) of tetraethyl methylenediphosphonate and 17.2 gm (0.2 mol) of methyl acrylate were mixed, and 10 ml of saturated sodium ethanolate solution were added drop by drop under agitation. The reaction temperature increased to 60° C. The additive reaction was completed by postheating to 80° C to 90° C for 2½ hours.

The reaction product was subject to vacuum fractionation. The main fraction of the ester obtained had a boiling point of 180° C to 188° C/0.4 Torr and a density of $n_D^{20}$ = 1,4510. The yield was 33%.

The ester obtained was subsequently saponified by refluxing for a long period of time with concentrated hydrochloric acid and the free acid was separated. The yield upon saponification was approximately 87%. In accordance with potentiometric titration, the molecular weight of the 1,1-diphosphonopropane-3-carboxylic acid of the formula

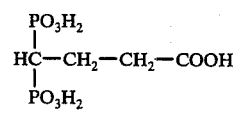

(I, R = H), obtained in the form of dihydrate, was 280.3 (calculated 284).

Analysis Values: Calculated: C 16.90% H 4.93% P 21.83%; Found: C 17.16% H 4.90% P 21.06%.

EXAMPLE 3

The acids of Examples 1 and 2 in aqueous solution were mixed with the stoichiometric amount of sodium hydroxide solution and evaporated to dryness to obtain, respectively:

Hexasodium 3,3-diphosphonate-pentane-1,5-dicarboxylate and

Pentasodium 1,1-diphosphonate-propane-3-carboxylate.

EXAMPLE 4

Threshold Effect - Modified Hampshire Test

The determining of the complex binding capacity by means of the modified Hampshire test, that is, the dissolving of freshly precipitated CaCO$_3$, clearly shows the efficacy of the new complex formers (III and IV).

The compounds I to IV utilized in the test were the following:

I 2-phosphono-butane-1,2,4-tricarboxylic acid
II 3-phosphono-pentane-1,3,5-tricarboxylic acid
III 3,3-diphosphono-pentane-1,5-dicarboxylic acid
IV 1,1-diphosphono-propane-3-carboxylic acid.

200 mgm of the sequestering agent were dissolved in 10 ml of H$_2$O (which has been adjusted with NaOH to pH11); and 100 ml of sodium carbonate solution (14.3 gm of Na$_2$CO$_3$ . H$_2$O/liter) were added. A calcium solution (36.8 gm of CaCl$_2$ . 2H$_2$O/liter) was added dropwise from a burette until the cloudiness formed barely remains. The results are given in Table I.

TABLE I

| Complex Former | MHT Values at pH 11 in gm-ions of Ca/Mol Acid |
|---|---|
| I | 1.60 |
| II | 1.26 |
| III | 2.91 |
| IV | 2.20 |

EXAMPLE 5

Threshold Effect - Carbonate/Silicate Test

The hardness-stabilizing effect in sub-stoichiometric quantities was determined at 60° C and 95° C in a sodium carbonate-silicate builder substance formulation.

25 ml of water having a German hardness of 80° C (Ca:Mg = 4:1) in a 100 ml graduated cylinder were treated with the sequestering agent solution (7.5 mgm or 15.0 mgm). After dilution with distilled water up to a volume of 65 to 70 ml, 25 ml of a sodium carbonate-sodium silicate solution having a concentration of 4.5 gm of $Na_2CO_3$/liter and 600 mgm of sodium silicate/liter (in a ratio of $SiO_2:Na_2O = 3.36:1$) were added. After filling up to the 100 ml mark, the sample was either heated to 60° C within 20 minutes and maintained at this temperature for an additional ten minutes (see Table II for the results of this procedure); or the sample was heated to 95° C within 25 to 30 minutes and maintained at 95° C for an additional 30 minutes. (See Table III for the results of this procedure.)

Subsequently, the solution, the precipitated portion, and the incrustation tightly adhering to the glass were analyzed as to their calcium content. In Table II and Table III, the results of the analyses are expressed in percent whereby the sum of the resulting values is set equal to 100%. The compounds employed are identified above in Example 4.

TABLE II

| | 150 mg/liter - 60° C | | |
|---|---|---|---|
| Complex Former | % CaO Dissolved | % CaO Precipitated | % CaO Incrustation |
| I | 98.8 | 1.0 | 0.2 |
| II | 27.4 | 54.7 | 17.9 |
| III | 100.0 | 0 | 0 |
| IV | 100.0 | 0 | 0 |

TABLE III

| | 150 mg/liter - 95° C | | |
|---|---|---|---|
| Complex Former | % CaO Dissolved | % CaO Precipitated | % CaO Incrustation |
| I | 98.9 | 0.9 | 0.2 |
| II | 6.1 | 4.4 | 89.5 |
| III | 100.0 | 0 | 0 |
| IV | 98.0 | 2.0 | 0 |

EXAMPLE 6

Pharmaceutical Preparations

For the production of pharmaceutical preparations in the form of a tablet, the known methods of preparation were followed to produce a tablet having an effective dosage unit composition as follows:

| Compound of Example 1 | 100 mgm |
|---|---|
| Lactose | 100 mgm |
| Starch | 47 mgm |
| Magnesium stearate | 3 mgm |

For the production of pharmaceutical preparations in the form of a capsule, the known methods of preparation are followed to produce a capsule having an effective dosage unit composition as follows:

| Compound of Example 2 | 100 mgm |
|---|---|
| Starch | 20 mgm |
| Sodium lauryl sulfate | 1 mgm |

The compounds of the invention are interchangeable in the above formulations. In another series of compositions, the free acids in the above formulations were replaced by the corresponding amounts of the tetrasodium or trisodium salts of the acids, respectively.

EXAMPLE 7

Cosmetic Preparations

The following recipes are suitable as a basic formula for toothpastes:

| | | Parts by Weight |
|---|---|---|
| (a) | Glycerin | 60.0 |
| | Water | 13.5 |
| | Sodium carboxymethyl-cellulose | 0.6 |
| | Silicic acid zerogel | 20.0 |
| | Sodium laurylsulfate | 2.0 |
| | Essential oils | 1.0 |
| | Sweetening agent | 0.4 |
| | Compound of Example 2 | 2.5 |
| (b) | Glycerin | 30.0 |
| | Water | 18.5 |
| | Sodium carboxymethyl-cellulose | 1.0 |
| | Aluminum hydroxide | 44.0 |
| | Sodium laurylsulfate | 1.0 |
| | Pyrogenic silicic acid | 1.5 |
| | Essential oils | 1.5 |
| | Sweetening agent | 0.5 |
| | Compound of Example 1 | 2.0 |

Suitable as a basic formulation for mouthwashes is the following recipe:

| | Parts by Weight |
|---|---|
| Ethyl alcohol | 19.5 |
| Glycerin | 7.5 |
| Water | 70.0 |
| Essential oils | 0.2 |
| Sodium laurylsulfate | 0.1 |
| Antiseptic (chlorothymol) | 0.1 |
| Sweetening agent | 0.1 |
| Compound of Example 2 | 2.5 |

The corresponding neutral salts such as the sodium salts can also be employed.

By regular use of the mouthwashes and/or toothpastes containing the above-mentioned diphosphonoalkane carboxylic acids, according to the invention, the formation of tartar could be considerably reduced. The formation of hard compact plaque on the teeth was to a great extent prevented.

The preceding specific embodiments are illustrative of the practice of the invention. It is to be understood, however, that other expedients known to those skilled in the art or discussed herein may be employed without departing from the spirit of the invention or the scope of the appended claims.

We claim:

1. A diphosphonoalkane carboxylic acid selected from the group consisting of (A) a compound of the formula

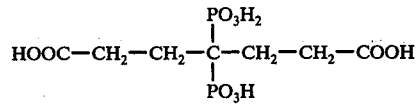

and (B) a non-toxic, pharmacologically-acceptable water-soluble salt thereof.

2. A process for the production of the diphosphonoalkane carboxylic acid of claim 1, consisting essentially of reacting a lower alkyl ester of acrylic acid with a lower alkyl ester of methylene diphosphonic acid in at least a 2:1 molar ratio in the presence of a strongly basic catalyst, saponifying the reaction product under aqueous acidic saponification conditions and recovering said diphosphonoalkane carboxylic acid.

* * * * *